United States Patent [19]

Awazu et al.

[11] Patent Number: 5,231,114
[45] Date of Patent: Jul. 27, 1993

[54] POLYSULFIDES COMPOUNDS AND LIPID PEROXIDATION INHIBITOR CONTAINING THE POLYSULFIDE COMPOUNDS AS ACTIVE INGREDIENT

[75] Inventors: Shoji Awazu, Kawaguchi; Toshiharu Horie, Musashimurayama; Yukihiro Kodera, Hiroshima; Shinji Nagae, Hiroshima; Hiromichi Matsuura, Hiroshima; Yoichi Itakura, Hiroshima, all of Japan

[73] Assignee: Wakunaga Seiyaku Kabushiki Kaisha, Osaka, Japan

[21] Appl. No.: 867,431

[22] Filed: Apr. 13, 1992

Related U.S. Application Data

[63] Continuation of Ser. No. 718,763, Jun. 21, 1991, Pat. No. 5,149,879.

[30] Foreign Application Priority Data

Jun. 22, 1990 [JP] Japan ................................. 2-165445

[51] Int. Cl.$^5$ .............................................. A01N 41/12
[52] U.S. Cl. ................................................. 514/707
[58] Field of Search ......................................... 514/707

[56] References Cited

U.S. PATENT DOCUMENTS 2,917,429 12/1959 Scott et al. .................. 514/707
3,103,465 9/1963 Goodhue et al. .
4,804,485 2/1989 Carrol et al. .
4,933,481 6/1990 Vallee et al. .

OTHER PUBLICATIONS

Itoh et al., Archives of Biochemistry and Biophysics, vol. 24, (1) 184–191, 1988.
Gut et al., Biochemica et Biophysica Aeta 817 (1985) 217–228.
Watabe et al. Biochemia et Biophysica Acta, 795 (1984) 60–66.
Dolands's Medical Dictionary, 26th edition.
Okada et al., Biochemistry et Biophysica Acta 922 (1987) 28–33.
Bull Chem. Soc Jpn. 52(10) 3117–3118 (1979) New Synthesis of Alkyl Polysulfides by Treatment of Thiols, Disulfides and Thionitrites with Anhydrous Copper(II) Chloride, Yong Hae Kim, Koichi Shinhama and Shigeru Oae.
Patent Abstracts of Japan, vol. 10, No. 131 (C-346) [2188], May 15, 1986, & JP-A-60 258 157, Dec. 20, 1985, J. Kominato, "Trisulfide Compound and Its Preparation".
Patent Abstracts of Japan, vol. 7, No. 61, (C-156) [1206], Mar. 5, 1983, & JP-A-57 209218, Dec. 22, 1982, T. Ariga, et al., "Antithrombotic".
Chemical Abstracts, 96652Y, vol. 111, No. 11, Sep. 11, 1989, p. 687, & JP-A-01 019057, Jan. 23, 1989, T. Hiramitsu, "Preparation of Allyl 1-Propenyl Disulfides as Garlic Flavor, Pharmaceuticals, and Agrochemicals".

Primary Examiner—Marianne M. Cintins
Assistant Examiner—Rebecca Cook
Attorney, Agent, or Firm—Oblon, Spivak, McClelland, Maier & Neustadt

[57] ABSTRACT

A lipid peroxidation inhibitor contains a polysulfide compound represented by formula (I) as an active ingredient:

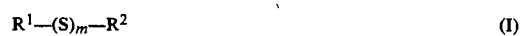

$$R^1-(S)_m-R^2 \qquad (I)$$

wherein $R^1$ and $R^2$ are same or different hydrocarbon chains having 1 to 16 carbon atoms and m is an integer of 3 to 10. Among compounds (I) are found novel which are:

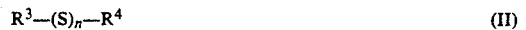

$$R^3-(S)_n-R^4 \qquad (II)$$

wherein $R^3$ and $R^4$ are same or different lower alkenyl groups and n is an integer of 6 to 10. Pharmaceutical compositions which contain a polysulfide compound represented by formula (I) as an active ingredient, for preventing and curing diseases of thrombosis, arteiosclerosis, liver troubles, pulmonary edema, skin troubles, eye troubles and aging are also disclosed.

2 Claims, 4 Drawing Sheets

POLYSULFIDES COMPOUNDS AND LIPID PEROXIDATION INHIBITOR CONTAINING THE POLYSULFIDE COMPOUNDS AS ACTIVE INGREDIENT

This is a continuation of application Ser. No. 07/718,763 U.S. Pat. No. 5,149,879, filed on Jun. 21, 1991.

BACKGROUND OF THE INVENTION i) Field of the Invention:

The present invention relates to polysulfide compounds and a lipid peroxidation inhibitor containing the polysulfide compounds as an active ingredient.

ii) Description of the Background Art:

It is well known that a variety of vital phenomena involve a lipid peroxidation reaction, which is initiated by a free radical reaction. In particular, if the chain reaction of free radical is not cut off, an oxygen radical, a so-called an active oxygen produced in any creature induces lipid peroxidation against lipids present as a basic material of a vital organism, for example, against polyvalent fatty acids constituting a matrix of a biomembrane.

That is, a lipid free radical and a peroxy free radical are produced in a series of steps to form a harmful peroxide lipid against the vital organism.

Hence, the lipid peroxidation reaction is concerned in a number of sicknesses or diseases, for instance, hemolytic anemia, various inflammations, myocardial infarction, cirrhosis of the liver, atherosclerosis and so forth, and further it is considered that this reaction participates carcinogenesis and aging.

Thus, for preventing and curing sicknesses and diseases due to such lipid peroxidation, development of drugs or pharmaceuticals for inhibiting the lipid peroxidation has been demanded. Some drugs for inhibiting the lipid peroxidation have been proposed, but cannot necessarily have sufficient efficiency.

Under the above circumstances, the present inventors have carried out researches for developing drugs or pharmaceuticals having a clinically excellent lipid peroxidation inhibiting effect and have found that a first group of polysulfide compounds having a formula (I):

$$R^1-(S)_m-R^2 \quad (I)$$

wherein $R^1$ and $R^2$ are same or different hydrocarbon chains having 1 to 16 carbon atoms and m is an integer of 3 to 10, which are obtained by an extraction from the Allium plants widely used as foods and drugs or pharmaceutical materials particularly garlic, scallion, elephant garlic or the like or a treated material thereof or by a chemical synthesis, possess an excellent lipid peroxidation inhibiting effect, and that a second group of polysulfide compounds included in the first group of the polysulfide compounds, having a formula (II):

$$R^3-(S)_n-R^4 \quad (II)$$

wherein $R^3$ and $R^4$ are same or different lower alkenyl groups and n is an integer of 6 to 10, are novel compounds.

SUMMARY OF THE INVENTION

Accordingly, it is an object of the present invention to provide a lipid peroxidation inhibitor containing polysulfide compounds represented by the following forumula (I) as an active ingredient:

$$R^1-(S)_m-R^2 \quad (I)$$

wherein $R^1$ and $R^2$ are same or different hydrocarbon chains having 1 to 16 carbon atoms and m is an integer of 3 to 10.

It is another object of the present invention to provide polysulfide compounds represented by the following formula (II):

$$R^3-(S)_n-R^4 \quad (II)$$

wherein $R^3$ and $R^4$ are same or different lower alkenyl groups and n is an integer of 6 to 10.

It is still another object of the present invention to provide a pharmaceutical composition containing polysulfide compounds represented by formula (I) as an active ingredient, for preventing and curing diseases of thrombosis, arteiosclerosis, liver troubles, pulmonary edema, skin troubles, eye troubles and aging.

The above and other objects, features and advantages of the present invention will more fully appear from the following description of the preferred embodiments with reference to the accompanying drawings.

DETAILED DESCRIPTION OF THE INVENTION AND PREFERRED EMBODIMENTS

Figure 1:
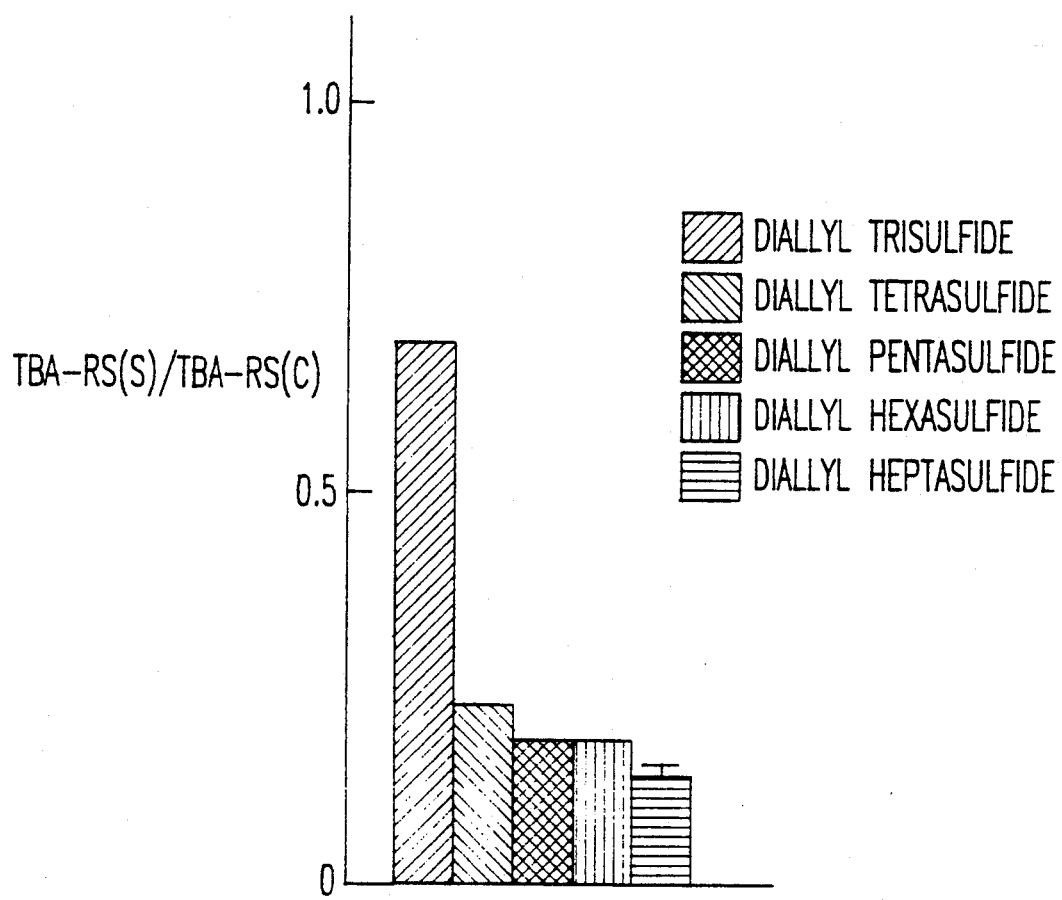
FIG. 1 is a graphical representation showing lipid peroxidation inhibiting effect by the ratio between thiobarbituric acid-reactive substances TBA-RS(S) and TBA-RS(C) of polysulfides of the present invention as index.

As to the hydrocarbon chains represented by $R^1$ and $R^2$ in formula (I), linear, branched or cyclic alkyl, alkenyl or alkynyl groups are given, and, in particular, lower alkyl, alkenyl or alkynyl groups are preferable. As examples of the lower alkyl groups, alkyl groups having 1 to 6 carbon atoms such as methyl, ethyl, n-propyl, hexyl, iso-propyl, tert.-butyl, cyclohexyl and the like are given. As examples of the lower alkenyl groups, alkenyl groups having 2 to 5 carbon atoms such as vinyl, allyl, 1-propenyl, iso-propenyl, 1,3-butadienyl and the like are given. As examples of the lower alkynyl groups, alkynyl groups having 2 to 5 carbon atoms such as 2-propynyl, 2-butynyl, 2-pentene-4-ynyl and the like are given. As to the lower alkenyl groups represented by $R^3$ and $R^4$ in general formula (II), the similar groups to the above-described alkenyl groups for $R^1$ and $R^2$ are given.

In formula (I), m is an integer of 3 to 10, and 3 to 8 are more preferable. In formula (II), n is an integer of 6 to 10, and 6 to 8 are more preferable.

As regards preferable examples of the compounds represented by formula (I), diallyl trisulfide, diallyl tetrasulfide, diallyl pentasulfide, diallyl hexasulfide, diallyl heptasulfide, diallyl octasulfide, methylallyl trisulfide, methylallyl tetrasulfide, methylallyl pentasulfide, methylallyl hexasulfide, methylallyl heptasulfide, di(1-propenyl) trisulfide, di(1-propenyl) tetrasulfide, di(1-propenyl) pentasulfide, di(1-propenyl) hexasulfide, di(tert.-butyl) tetrasulfide, di(tert.-butyl) pentasulfide, allylvinyl tetrasulfide, allyl tert.-butyl tetrasulfide and the like are given.

As to preferable examples of the compounds represented by general formula (II), diallyl hexasulfide, diallyl heptasulfide, diallyl octasulfide, allylvinyl hexasulfide, allyl 1-propenyl hexasulfide and the like are given.

The polysulfide compounds represented by formula (I), to be used in the present invention, can be produced by either an extraction from the Allium plants or a chemical synthesis.

The Allium plants to be used for the extraction are plants included in the Allium genus of the Liliaceae family, and more specifically, garlic (Allium sativum), scallion (Allium chinense or Allium Bakeri Regel), elephant garlic (Allium ampeloprasum) and the like.

The extraction can be carried out from the whole plant, preferably, from bulbs containing divided semispherical or bowllike. Also, a cell lump obtained by a tissue culture or other methods, a callus, a regenerated plant can be used.

The extraction method is not restricted, and this treatment may be carried out by any conventional techniques commonly used in the exaction of crude drugs. That is, the extraction can be carried out by immersing the plant in water or an organic solvent mixible with the water. Regarding the organic solvent used as an extraction treating solvent, lower alcohols, for example, monovalent alcohols having 1 to 3 carbon atoms can be used, and particularly ethanol is preferable. In the extraction, as a matter of course, a crushed or disintegrated plant is preferably used in order to improve the efficiency.

The polysulfide compounds represented by formula (I) are nonpolar materials produced in the extraction and are not only contained in the extracted solution but also adsorbed by the residue. The extraction of the polysulfide compounds from the residue can be carried out by immersing the residue in an organic solvent including or excluding the water or by the steam distillation. In this case, as examples of the organic solvent to be used as an extractant, lower alcohols, acetone and the like as a solvent mixible with the water and chloroform, ethyl acetate, hexane and the like as a solvent unmixible with the water are given. In these solvents, particularly preferable solvents are ethyl acetate, chloroform and hexane.

The extractant is removed from the obtained extracted solution by distillation, or the water is added to the extracted solution so as to extract with an organic solvent capable of partitioning the water to obtain the extract. The extract is appropriately separated by the chromatography using a normal phase adsorbent (preferably silica gel) or a reversed phase adsorbent to obtain polysulfide compounds.

On the other hand, a production of polysulfide compounds by chemical synthesis is performed by reacting, for example, diallyl disulfide with cupric chloride-ferric chloride and the like as a catalyst at room temperature, as disclosed in "Organic Sulfur Chemistry" ("Volume: Synthetic Reaction"), p. 98, by Shigeru OAE, Kagaku Dojin, 1982.

The polysulfide compounds represented by formula (I), obtained as described above, exhibit an excellent lipid peroxidation inhibiting effect within tissue of a liver microsome, blood or the like. Further, since these compounds are the extract naturally occurring from the plant such as garlic or the like or analogous plants, the safety is high. Hence, the polysulfide compounds represented by formula (I) as a lipid peroxidation inhibitor can be utilized for prevention or cure of a variety of diseases or sicknesses such as thrombosis, arteiosclerosis, liver trouble, pulmonary edema, skin trouble, eye trouble and aging.

According to the present invention, a lipid peroxidation inhibitor contains at least one polysulfide compound represented by formula (I) as an active ingredient. The lipid peroxidation inhibitor can be mixed with a liquid or solid pharmaceutically acceptable preparational auxiliary components or carriers such as excipients, binders, diluents and the like to form any drug form such as powders, granules, tablets, capsules, liquids and injections, and can be administrated orally or parenterally.

The dose of the lipid peroxidation inhibitor is properly varied depending upon age, weight, symptom and so forth. The oral dose for adult in terms of polysulfide compounds represented by formula (I) is preferably 1 mg to 10 g per day, which can be administrated in one time or divided into several times. As a matter of course, when the lipid peroxidation inhibitor is administrated, it can be mixed with another drug, as required.

Then, the examplary embodiments of the present invention will now be described in detail, and it should be understood that these embodiments are given for illustration of the invention and are not intended to be limitative therefor.

EXAMPLE 1

Production of diallyl polysulfide compounds from garlic:

10 kg of garlic was crushed and extracted with 10 l of 20% ethanol at room temperature. After the solid was separated from the solution, the extracted solution was concentrated under reduced pressure, and water was added to the solution. The extraction was carried out by 5 l of ethyl acetate. On the other hand, the residue was extracted by 5 l of ethyl acetate. The obtained extracted solution was mixed with the previously obtained ethyl acetate extracted solution, and the mixed extracted solution was concentrated under reduced pressure to obtain an extract. The obtained extract was treated by a silica gel column chromatography with n-hexane as a solvent. The obtained sulfide fraction was separated by high performance liquid chromatography (TSK gel ODS 80TM (TOSOH), 90% ethanol eluate) to obtain 81 mg of diallyl trisulfide, 154 mg of diallyl tetrasulfide, 102 mg of diallyl pentasulfide, 48 mg of diallyl hexasulfide and 11 mg of diallyl heptasulfide.

Data of the obtained polysulfides are shown as follows:

(1) Diallyl trisulfide:
1) External appearance: slightly yellow oil
2) $^1$H-NMR (deuterochloroform) δ: 3.51(2H, d,J=7.0 Hz), 5.2–5.3(2H,m), 5.8–6.0(1H,m)

3) $^{13}$C-NMR (deuterochloroform) δ: 41.7, 119.1, 132.7

4) High Resolution Mass Spectra: as $C_6H_{10}S_3$ Theoretical value: 177.995; Measured Value: 177.997

(2) Diallyl tetrasulfide:
1) External appearance: slightly yellow oil
2) $^1$H-NMR (deuterochloroform) δ: 3.59(2H,d,J=7.3 Hz), 5.2–5.3(2H,m), 5.8–6.0(1H,m)
$^{13}$C-NMR (deuterochloroform) δ: 42.1, 119.5, 132.5
4) High Resolution Mass Spectra: as $C_6H_{10}S_4$ Theoretical value: 209.962; Measured Value: 209.964

(3) Diallyl pentasulfide:
1) External appearance: slightly yellow oil
2) $^1$H-NMR (deuterochloroform) δ: 3.61(2H, d, J=7.3 Hz), 5.2–5.3(2H, m), 5.8–6.0(1H, m)
3) $^{13}$C-NMR (deuterochloroform) δ: 42.6, 119.8, 132.2
4) High Resolution Mass Spectra: as $C_6H_{10}S_5$ Theoretical value: 241.938; Measured Value: 241.938

(4) Diallyl hexasulfide:
1) External appearance: slightly yellow oil
2) $^1$H-NMR (deuterochloroform) δ: 3.62(2H, d, J=7.3 Hz), 5.2–5.3(2H, m), 5.8–6.0(1H, m)
3) $^{13}$C-NMR (deuterochloroform) δ: 42.5, 120.0, 132.2
4) High Resolution Mass Spectra: as $C_6H_{10}S_6$ Theoretical value: 273.915; Measured Value: 273.913

(5) Diallyl heptasulfide:
1) External appearance: slightly yellow oil
2) $^1$H-NMR (deuterochloroform) δ: 3.62(2H, d, J=7.3 Hz), 5.2–5.3(2H, m), 5.8–6.0(1H, m)
3) $^{13}$C-NMR (deuterochloroform) δ: 42.5, 120.0, 132.2
4) High Resolution Mass Spectra: as $C_6H_{10}S_7$ Theoretical value: 305.885; Measured Value: 305.884

EXAMPLE 2

Production of diallyl polysulfide compounds from diallyl disulfide:

55 g of anhydrous ferric chloride was dissolved in 400 ml of ether, and in this ethyl ether solution was added a solution where 11.5 g of anhydrous cupric chloride was dissolved in 400 ml of acetonitrile. In this mixture, 25 g of diallyl disulfide was added, and stirred overnight in a stream of nitrogen at room temperature while the light was shielded. The reaction mixture was poured into 400 ml of saturated sodium chloride aqueous solution, and extracted four times by 400 ml of n-hexane. Then, the obtained n-hexane layer dehydrated by anhydrous sodium sulfate, and was then concentrated under reduced pressure. The obtained sulfide fraction was separated by high performance liquid chromatography (TSK gel ODS 80TM (TOSOH), 90% ethanol eluate) to obtain 90 mg of diallyl trisulfide, 81 mg of diallyl tetrasulfide, 75 mg of diallyl pentasulfide, 46 mg of diallyl hexasulfide and 36 mg of diallyl heptasulfide.

TEST EXAMPLE 1

Lipid peroxidation inhibiting effect:
1) Test method:
Lipid peroxidation inhibiting effect of the polysulfide compounds represented by formula (I) in liver microsomes was examined by using the formation of thiobarbituric acid-reactive substances (TBA-RS) and fluorescent substances as index.

That is, liver microsomes (see F. Itoh et al., Arch. Biochem. Biophys. 264, 184(1988)) prepared from male Wistar rats were incubated for 5 minutes at 37° C. in the presence or absence of the polysulfide compound, and then 0.1 mM of ascorbic acid and 5 μM of ferrous sulfate were added to the microsome suspension to initiate lipid peroxidation. The mixture was incubated for 3 hours at 37° C. The reaction was terminated by adding 1 mM of EDTA.

i) Assay of thiobarbituric acid-reactive substances (TBA-RS):
An assay of malondialdehyde produced by the lipid peroxidation was carried out by the method of Buege et al. (Methods Bnzymol., 52, 302(1978)).

ii) Measurement of fluorescent substances:
After the termination of the lipid peroxidation, the microsomes were separated by Sephadex G-25 column chromatography by using 0.1M of sodium phosphate buffer solution containing 1 mM of EDTA. The fluorescence emitted by the obtained peroxidized microsome was measured by the direct method (see F. Itoh et al., Arch. Biochem. Biophys., 264, 184 (1988)).

Figure 2:
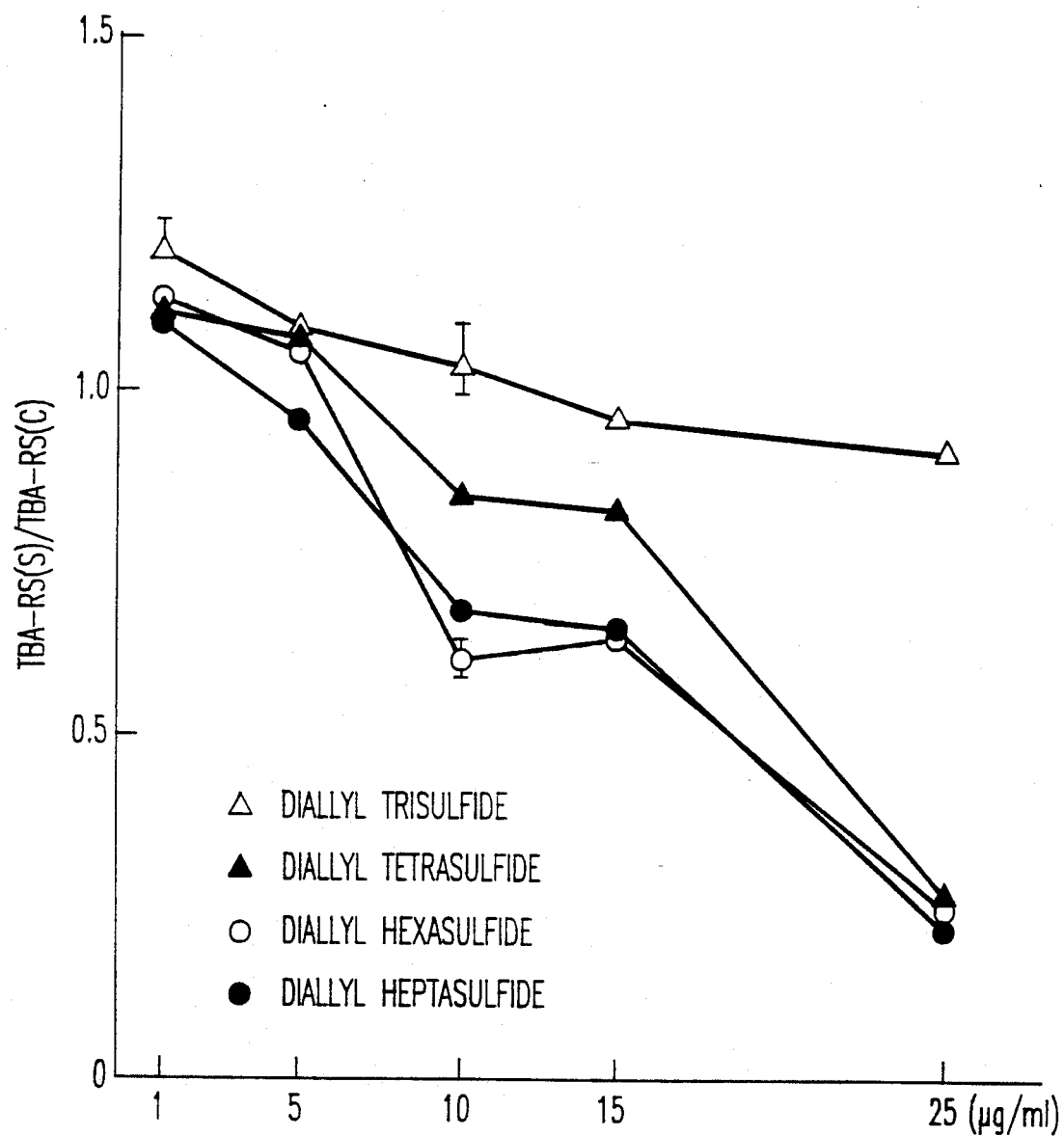
FIG. 2 is a graphical representation showing lipid peroxidation inhibiting effect by the ratio between the thiobarbituric acid-reactive substances TBA-RS(S) and TBA-RS(C) with reference to sample concentrations of 1 to 25 μg/ml.
Figure 3:
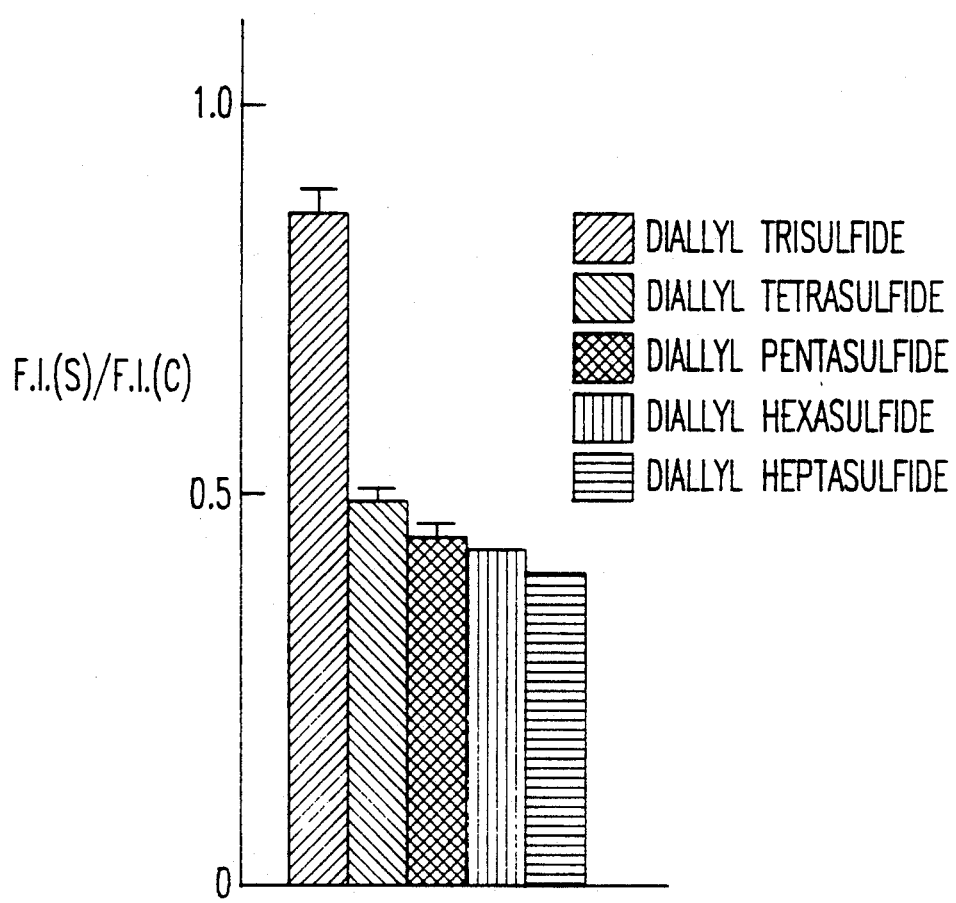
FIG. 3 is a graphical representation showing lipid peroxidation inhibiting effect by a ratio between fluorescence intensities F.I.(S) and F.I.(C) of polysulfides of the present invention as index.
Figure 4:
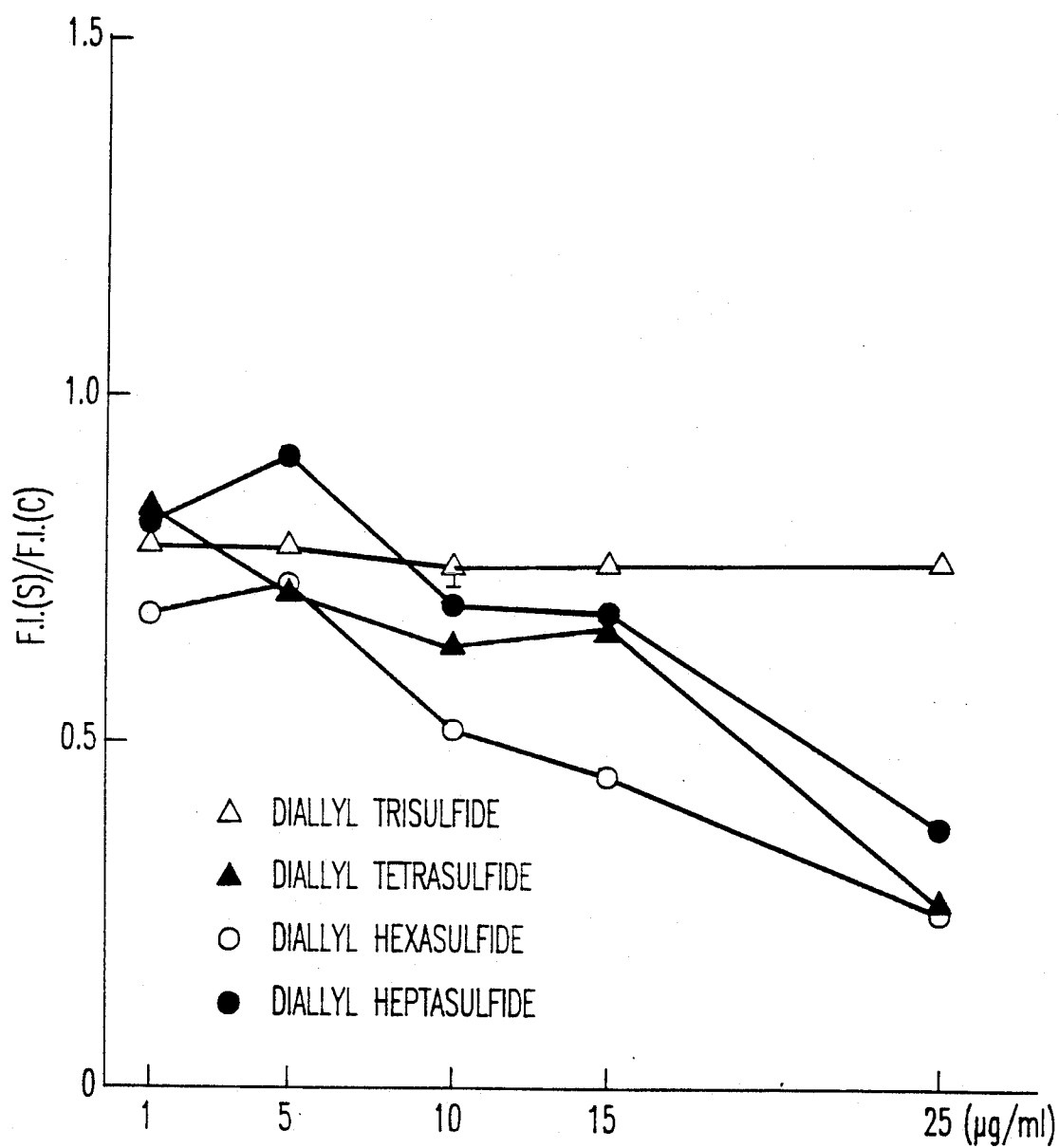
FIG. 4 is a graphical representation showing lipid peroxidation inhibiting effect by the ratio between the fluorescence intensities F.I.(S) and F.I.(C) of polysulfides of with reference to sample concentrations of 1 to 25 μg/ml.

2) Results:
i) The formation of the TBA-RS as the index of lipid peroxidation was determined in the presence and absence of the polysulfide compound to obtain TBA-RS(S) and TBA-RS(C), respectively. A sample concentration was determined to be 25 μg/ml, and a ratio TBA-RS(S)/TBA-RS(C) between the TBA-RS(S) and TBA-RS(C) was obtained. As a result, a TBA-RS inhibiting effect was observed in the polysulfide compounds, as shown in FIG. 1. Further, when the sample concentration was varied to 1, 5, 10, 15 and 25 μg/ml, the ratio TBA-RS(S)/TBA-RS(C) for each compound was obtained, and as a result, a concentration dependence was clearly observed, as shown in FIG. 2.

ii) It is well known that with the lipid peroxidation, fluorescent substances were produced. By using the formation of fluorescent substances as the index, a ratio F.I.(S)/F.I.(C) between fluorescent intensities F.I.(S) and F.I.(C) was obtained in the presence and absence of the polysulfide compound. As a result, it was observed that the polysulfide compounds inhibit the formation of the fluorescent substances, as shown in FIG. 3. Further, when the sample concentration was varied to 1, 5, 10, 15 and 25 μg/ml, the fluorescent intensity ratio F.I.(S)/F.I.(C) for each compound was obtained, and as a result, a concentration dependence was clearly observed, as shown in FIG. 4.

As described above, it was observed that the polysulfide compounds have a remarkable lipid peroxidation inhibiting effect.

According to the present invention, lipid peroxidation inhibitors containing the polysulfide compounds represented by formula (I) as an active ingredient are effective for the prevention and cure of a variety of diseases or sicknesses due to lipid peroxidation, which include, thrombosis, arteiosclerosis, liver troubles, pulmonary edema, skin troubles, eye troubles and aging.

Although the present invention has been described in its preferred embodiments, it is readily understood that the present invention is not restricted to the preferred embodiments and that various changes and modifications thereof can be made by those skilled in the art without departing from the spirit and scope of the present invention.

What is claimed is:
1. A method of inhibiting lipid peroxidation in a patient in need thereof comprising administering a lipid peroxidation inhibiting effective amount of a lipid peroxidation inhibitor comprising:

a polysulfide compound of formula (I) as the active ingredient $$R^1-(S)_m-R^2 \quad (I)$$

wherein $R^1$ and $R^2$ are the same or different hydrocarbon chains having 1 to 16 carbon atoms and m is an integer of 3 to 10; and a pharmaceutically acceptable carrier.

2. The method of claim 1, wherein $R^1$ and $R^2$ are the same or a different lower alkenyl groups and m is an integer of 3 to 10.

* * * * *